United States Patent [19]

Nakamura et al.

[11] Patent Number: 4,768,757
[45] Date of Patent: Sep. 6, 1988

[54] APPARATUS FOR NITRIDING SURFACE OF SHAPED ARTICLE OF TITANIUM

[75] Inventors: Seizo Nakamura, Osaka; Yoshiichi Tsutsui, Sakai, both of Japan

[73] Assignee: Ohara Co., Ltd., Osaka, Japan

[21] Appl. No.: 18,312

[22] Filed: Feb. 24, 1987

[30] Foreign Application Priority Data

Feb. 24, 1986 [JP] Japan .................................. 61-38641
Jun. 20, 1986 [JP] Japan ................................ 61-145671

[51] Int. Cl.$^4$ ............................................... C71D 9/00
[52] U.S. Cl. ..................................... 266/252; 266/274
[58] Field of Search ................ 266/249, 274, 287, 252

[56] References Cited

U.S. PATENT DOCUMENTS 4,528,043 7/1985 Mills .................................... 148/13.1

OTHER PUBLICATIONS

Journal of the Japan Institute of Metals, vol. 43, No. 10, 938–947, (1979).

The Journal of the Japanese Society for Dental Material and Device, vol. 3, No. 1, 71–78, (1984).

Primary Examiner—Christopher W. Brody
Attorney, Agent, or Firm—Armstrong, Nikaido, Marmelstein & Kubovcik

[57] ABSTRACT

A nitride layer is formed on the surface of a shaped article of titanium by a method which comprises bringing nitrogen gas into contact with the shaped article of titanium in a heated state. The nitrogen gas, en route to the site of contact with the shaped article of titanium, is preparatorily caused to come into contact and react with small particles of titanium so as to be deprived of such extraneous components as hydrogen and oxygen and consequently converted into pure nitrogen gas. This pure nitrogen gas is introduced into contact with the shaped article of titanium in a heated state to effect the nitriding of the surface of the shaped article. An apparatus to be used in effecting the nitriding treatment by the method of this invention is also disclosed.

12 Claims, 5 Drawing Sheets

APPARATUS FOR NITRIDING SURFACE OF SHAPED ARTICLE OF TITANIUM

BACKGROUND OF THE INVENTION

1. Field of the Invention

This invention relates to a method for nitriding the surface of a shaped article of titanium such as a dental cast and to an apparatus for the nitriding treatment.

2. Description of the Prior Art

In recent years, use of products by the casting of pure titanium or titanium alloys is disseminating in the field of dentistry. In consequence of this trend, the practice of nitriding the surface of such a shaped article of titanium as described above thereby forming a nitride layer on the surface to increase the surface hardness and improve the abrasion resistance of the surface and, at the same time, conferring a golden color upon the surface to give an added value to the shaped article is gaining growing acceptance. Further, this nitriding treatment for shaped articles of titanium is used on industrial parts in general similarly for the purpose of increasing surface hardness and improving abrasion resistance. As means for providing nitrided surfaces for shaped articles of titanium, there have been known the gas nitriding method and the ion nitriding method. For example, Japanese Patent Publication SHO 56(1981)-44,148 discloses a method for nitriding the surface of a shaped article of titanium or an α-titanium alloy. This surface nitriding method comprises keeping a shaped article of pure titanium or an α-titanium alloy in contact with a titanium nitride powder in a chamber and feeding nitrogen gas into the chamber and heating the contents of the chamber at a temperature approximately in the range of 790° to 880° C. thereby causing the titanium nitride powder enveloping the shaped article of titanium to nitride the surface of the shaped article. This method, however, has a disadvantage that the nitriding treatment takes a long time because the formation of a nitride on the surface of the shaped article of titanium relies on the mutual reaction between the titanium nitride and the shaped article of pure titanium or an α-titanium alloy. As another means, the gas nitriding method has been known to the art which comprises bringing nitrogen gas into contact with a shaped article of titanium as kept in a heated state. This method effects the surface nitriding treatment by the action of nitrogen gas of high purity. Despite its high purity, the nitrogen gas inevitably contains impurities such as oxygen and nitrogen even in minute amounts. When the surface of a shaped article of pure titanium or a titanium alloy is exposed to the nitrogen gas, therefore, these impurities react with the surface to induce such adverse conversions as oxidation and absorption of hydrogen and tend to impede uniform deposition of a nitride layer on the surface of the shaped article of titanium, impair the surface strength, or cause the surface of the shaped article of titanium to assume a color different from the color desired. Removal of such extraneous oxygen and hydrogen components from the nitrogen gas necessitates use of an apparatus which is voluminous and very costly. The apparatus, therefore, constitutes a cause for obstruction in the general sense of cost reduction and enhanced adaptability.

SUMMARY OF THE INVENTION

An object of this invention is to provide a method for nitriding the surface of a shaped article of pure titanium or a α-titanium alloy, which method effects the nitriding treatment inexpensively and expediently as compared with the conventional method necessitating use of an expensive and complicated apparatus and enables the nitriding treatment to be completed in a short time, and an apparatus to be used in performing the nitriding treatment by the method of this invention. To be specific, this invention effects formation of a uniform nitride layer on the surface of a shaped article of pure titanium or a titanium alloy by a method which comprises causing the nitrogen gas which is destined to contact the shaped article of pure titanium or a titanium alloy and form a nitride layer on the surface of the shaped article preparatorily to contact small particles of pure titanium or a titanium alloy thereby depriving the nitrogen gas of such extraneous components as oxygen and hydrogen through reaction thereof with the small particles of pure titanium or titanium alloy and consequently converting the nitrogen gas into pure nitrogen gas and subsequently allowing the pure nitrogen gas to come into contact with the aforementioned shaped article of titanium. An apparatus to be used in performing the aforementioned nitriding treatment of the surface of the shaped article of titanium by the method of this invention comprises one gas flow means extending between an inlet connected to a nitrogen gas supply means and an outlet adapted to effect discharge of a gas related to a vacuum means, a nitrogen gas filter incorporating therein small particles of pure titanium or a titanium alloy and a part for disposing a shaped article of titanium for a nitriding treatment, the nitrogen gas filter and the shaped article disposing part disposed either independently of each other or as superposed one over the other inside the aforementioned flow means, and heating means disposed separately to serve the nitrogen gas filter and the shaped article disposing part, whereby the nitrogen gas caused to flow continuously by the nitrogen gas supply means and the vacuum means is heated by the heating means and, in a heated state, brought into contact with the small particles of pure titanium or a titanium alloy incorporated in the nitrogen gas filter to effect removal therefrom of the extraneous components such as hydrogen or oxygen through reaction with the small particles of pure titanium or titanium alloy and the nitrogen gas emanating in a purified state from the nitrogen gas filter is brought into contact, in a heated state, with the surface of the shaped article of titanium disposed in the shaped article disposing part so as to form a nitride layer on the surface and give rise to a nitrided shaped article of titanium.

The other objects and characteristic features of the present invention will become apparent to those skilled in the art as the disclosure is made in the following description of preferred embodiments of the invention, as illustrated in the accompanying drawings.

DETAILED DESCRIPTION OF THE INVENTION

This invention produces a nitride layer on the surface of a shaped article of pure titanium or a titanium alloy by introducing nitrogen gas into contact with small particles of pure titanium or small particles of a titanium alloy, preferably the small particles of pure titanium, thereby causing the extraneous components such as hydrogen and oxygen contained in the nitrogen gas to react with the small particles of pure titanium and separate from the nitrogen gas and subsequently advancing the nitrogen gas, now in a purified state, into contact with the surface of the shaped article of titanium under treatment in a heated state. The small particles of pure titanium or the small particles of a titanium alloy to be used in the procedure described above are generally required to have size and shape enough to avoid being burnt on contact with the nitrogen gas. Since the nitriding generally begins to proceed in the neighborhood of 700° C., the size of the small particles must be such that at temperatures of this neighborhood, the small particles of pure titanium or the small particles of a titanium alloy avoid commencing combustion on contact with the oxygen component contained in the nitrogen gas. It has been confirmed that in the case of the small particles of pure titanium, this size meeting the requirement just mentioned is about 100 mesh. The small particles of titanium having diameters smaller than 100 mesh, specifically diameters of about 150 mesh or 200 mesh, for example, tend to commence combustion on contact with the nitrogen gas. Such small particles of titanium having diameters smaller than 100 mesh which are liable to commence combustion on contact with the nitrogen gas heated to a temperature exceeding the aforementioned nitriding temperature, i.e. about 700° C., therefore, are to be exluded. Preferably, the small particles of titanium having diameters larger than 80 mesh are used herein. The size just mentioned is capable of precluding the small particles of titanium from commencing combustion on contact with the oxygen and hydrogen components present in the nitrogen gas even when this contact is made in a heated state. Small particles of sponge titanium are available at a rather low price and possess a relatively high porosity and a large surface area and make a satisfactory material for the removal of oxygen and hydrogen. Use of these small particles of sponge titanium, therefore, permits the nitriding of the surface of a shaped article of titanium to be attained inexpensively and efficiently. Optionally, the small particles of pure titanium or the small particles of a titanium alloy may be densely disposed along the periphery of the shaped article of titanium inside the treating part in the form of an empty space. In this setup, for the purpose of enabling the nitrogen gas to permeate the mass of the small particles of pure titanium or a titanium alloy and come readily into contact with the shaped article of titanium, these particles of titanium are desired not to be unduly small and, in the form of a mass, to exhibit high perviousness to gas and enable the nitriding treatment to be completed in a short span of time. In this sense, when the particles of titanium have diameters larger than 60 mesh, particularly diameters on the order of 35 mesh, they show the stability to avoid commencing combustion on contact with the nitrogen gas because the temperature of titanium in the initial stage of nitriding is about 700° C. and the heat distorsion point of titanium is slightly below 900° C.

Figure 1:
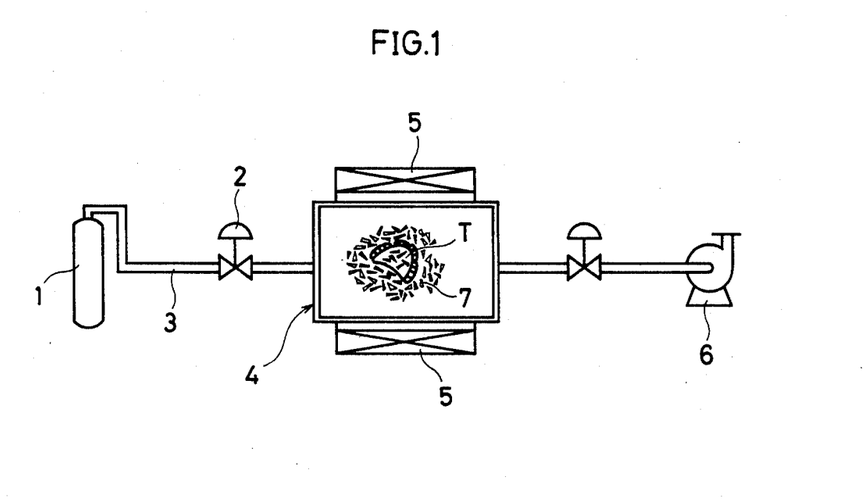
FIG. 1 is an explanatory process diagram illustrating a typical procedure for nitriding the surface of a shaped article of titanium as one embodiment of the present invention.
Figure 2:
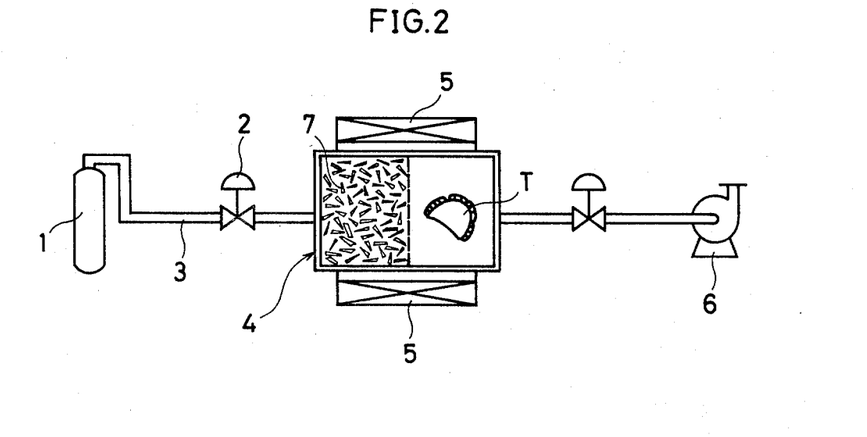
FIG. 2 is an explanatory flow diagram illustrating another procedure for the nitriding treatment mentioned above.

Now the present invention will be described more specifically below with reference to the explanatory process diagrams attached hereto. FIG. 1 depicts a typical procedure for nitriding the surface of a shaped article of titanium according to the present invention. A nitorgen gas cylinder 1 supplies nitrogen AgAS. When a valve 2 is opened, the nitrogen gas from the cylinder 1 can be supplied via a feed conduit 3 to the interior of an electric furnace as a titanium treating part 4. This electric furnace permits heating 5 required for a nitriding treatment and, at the same time, gives rise to a tightly closable chamber capable of establishing a nitriding atmosphere therein. To facilitate continuous supply of the nitrogen gas, a vacuum pump 6 located as shown in the diagram is adapted to draw out the inner gas of the treating part 4 in the opposite direction from the treating part 4. In this setup there is formed a flow path permitting supply of fresh gas from the nitrogen gas cylinder 1. Then, inside the electric furnace, a shaped article of titanium T, i.e. a shaped article of pure titanium or a titanium alloy to be treated, is disposed and small particles 7 of pure titanium or small particles 7 of a titanium alloy are disposed around the periphery of the shaped article of titanium. The nitrogen gas supplied from the nitrogen gas cylinder 1 fills up the interior of the electric furnace holding its contents as described above. The nitrogen gas thus filling the electric furnace is drawn out in the opposite direction by the vacuum pump 6. Thus, the interior of the electric furnace is always swept by a fixed volume of fresh nitorgen gas. When the electric furnace is set operating in the existent condition, the heating 5 is effected to elevate the inner temperature of the electric furnace or the treating part 4 to a predetermined level exceeding 700° C., for example, necessary for the nitriding reaction. In this case, the oxygen and nitrogen components present in the nitrogen gas supplied from the nitrogen gas cylinder 1 are brought into contact and allowed to react with the small particles 7 of pure titanium or the small particles 7 of a titanium alloy disposed around the periphery of the shaped article T of titanium while the nitrogen gas is en route to the shaped article T of titanium. The fresh nitrogen gas resulting from the separation of the oxygen and hydrogen components is then allowed to come into contact with the shaped article of titanium and, in a heated state, enabled to react with the surface of the shaped article of titanium and form a nitride layer on the surface. This operation is continued until the nitride layer grows to a desired thickness. In the setup illustrated in FIG. 2, the small particles 7 of pure titanium or the small particles 7 of a titanium alloy are not disposed around the periphery of the shaped article T of titanium as illustrated in FIG. 1 but are disposed in a part separated from a part for disposing the shaped article T of titanium. To be more specific, the small particles 7 of pure titanium or the small particles 7 of a titanium alloy are disposed at a suitable place in the nitrogen gas feed conduit 3 emanating from the nitrogen gas cylinder 1. In the illustrated setup, for example, the small particles 7 of pure titanium or the small particles 7 of a titanium alloy are disposed on the nitorgen gas inlet side of the electric furnace. As the nitrogen gas is passed through the interior of the electric furnace, the oxygen and hydrogen components present in the nitrogen gas are allowed to react with the small particles 7 of pure titanium or the small particles 7 of a titanium alloy. The nitrogen gas departing from the electric furnace in a purified state is brought into contact with the shaped article T of titanium and enabled to nitride the surface of the shaped article. Even in this setup, when the inner gas of the electric furnace is kept drawn out by the vacuum pump 6 and discharged to the righthand side in the illustrated bearings in much the same manner as in the setup of FIG. 1, the surface of the shaped article of titanium can be nitrided as desired. The airtightness of the treating part 4 can be easily maintained by keeping the pressure of nitrogen gas inside the treating part 4 slightly above the atmospheric pressure. At the outset of the operation of the apparatus, the creation of the airtight condition can be attained by first evacuating the interior of the electric furnace to a high degree of vacuum with the vacuum pump 6 and then introducing the nitrogen gas into the electric furnace thus held in a vacuumized state or by advancing the flow of the nitrogen gas into the electric furnace of the outset of the reaction and allowing the displacement of the inner gas of the electric furnace with the nitrogen gas to continue until the interior of the electric furnace is filled solely with the nitrogen gas. The heating may be effected after the interior of the electric furnace is filled solely with the nitrogen gas. Otherwise, the inner temperature of the electric furnace may be elevated to the prescribed level in advance and the shaped article of titanium as a member for treatment may be inserted into the furnace held in the heated state and, thereafter, the supply of the nitrogen gas may be started.

EXPERIMENT 1

Small particles of titanium of varying sizes were subjected to the nitriding treatment by the method described above to find temperatures at which they commenced combustion. The results are shown in Table 1. By this experiment, it has been demonstrated that small particles of titanium having a diameter of 100 mesh, for example, can be used at temperatures to exceeding 700° C. by the method of the present invention. In one test run, they formed a nitride layer $1\mu$ in thickness in four hours' treatment, for example. When small particles of titanium having a diameter of 100 mesh were subjected to the treatment at a higher temperature of 800° C., however, they occasionally commenced combustion. In this case, a nitride layer having a thickness of $2.5\mu$ was obtained in 4 hours' treatment. It has been found, consequently, that the small particles of a diameter of 100 mesh do not tolerate use in the treatment at temperatures exceeding 800° C. Then, the small particles of titanium having a diameter of 80 mesh could be used at a temperature of 850° C. and could not tolerate the treatment at 900° C., at which temperature they occasionally commenced combustion. It has been found that, since the heat distorsion point of titanium is about 882° C., the small particles of titanium are usable in the neighborhood of 900° C. only when they have a larger diameter of 60 mesh. Thus, it has been found that since the temperature generally used for the nitriding treatment falls in the range of 700° C. to 880° C., the small particles of titanium are effectively usable when they have a diameter of not less than 60 mesh. As regards the shape of the small particles of titanium, when small falkes of titanium resembling shavings are used and disposed around the periphery of the shaped article of titanium, since they are highly pervious to gas and are capable of easily binding with the oxygen and hydrogen components present in the nitrogen gas, they prove desirable for the formation of a nitride layer of desirable quality as compared with small particles of titanium in the form of beads or granules.

TABLE 1

| Size of small particles of titanium (mesh) | Temperature of nitriding treatment (°C.) | | | |
| --- | --- | --- | --- | --- |
| | 700 | 800 | 850 | 900 |
| 100 | Usable | Occasional combustion | Occasional combustion | Occasional combustion |
| 80 | Usable | Usable | Occasional combustion | Occasional combustion |
| 60 | Usable | Usable | Usable | Occasional combustion |
| 35 | Usable | Usable | Usable | Usable |
| Flakes | Usable | Usable | Usable | Usable |

EXPERIMENT 2

Small particles of sponge titanium or sponge titanium alloy of varying sizes were subjected to the nitriding treatment to find temperatures at which they commenced combustion. The results are shown in Table 2. By this experiment, it has been found that small particles of sponge titanium having a diameter of 100 mesh, for example, are usable effecitvely by the method of this invention at a temperature of 700° C. In one test run, they formed a nitride layer $1\mu$ in thickness in four hours' treatment. When the small particles of a diameter of 100 mesh were used at a higher temperature of 800° C., however, they occasionally were found to commence combustion. In this case, they produced a nitride layer $2.5\mu$ in thickness in four hours' treatment. It has been found, consequently, that the small particles of sponge titanium having a diameter of 100 mesh are not usable at temperatures exceeding 800° C. The small particles of sponge titanium having a diameter of 80 mesh could be used at a temperature of 850° C. At higher temperatures in the neighborhood of 900° C., however, they were not usable because they occasionally commenced combustion. It has been found that in the neighborhood of 900° C., since the heat distorsion temperature of titanium is about 882° C., the small particles of sponge titanium are usable only when they have a diameter larger than 60 mesh. It has further been found that since the temperature used for the nitriding treatment generally falls in the range of about 700° C. to 880° C., the small particles of sponge titanium are effectively usable when they have a diameter larger than 60 mesh.

TABLE 2

| Size of small particles of sponge titanium | Temperature of nitriding treatment (°C.) | | | |
| --- | --- | --- | --- | --- |
| | 700 | 800 | 850 | 900 |
| 100 mesh | Usable | Occasional | Occasional | Occasional |

TABLE 2-continued

| Size of small particles of sponge titanium | Temperature of nitriding treatment (°C.) | | | |
|---|---|---|---|---|
| | 700 | 800 | 850 | 900 |
| 80 mesh | Usable | combustion Usable | combustion Occasional combustion | combustion Occasional combustion |
| 60 mesh | Usable | Usable | Usable | Occasional combustion |
| 35 mesh | Usable | Usable | Usable | Usable |
| Cubes of 2 mm | Usable | Usable | Usable | Usable |
| Cubes of 6 mm | Usable | Usable | Usable | Usable |
| Cubes of 20 mm | Usable | Usable | Usable | Usable |

EXPERIMENT 3

Small particles of titanium produced in varying shapes were treated by the typical procedure of FIG. 1 under the conditions of 800° C. of temperature and 4 hours of duration. The results were as shown in the righthand column of Table 3. From the table, it is noted that the small particles of titanium having such small diameters as 200 mesh and 325 mesh do not tolerate actual use because they undergo the phenomenon of combustion. It has been found that the small particles of titanium having a diameter of 100 mesh are usable despite their liability to occasional combustion, indicating that this particular diameter constitutes the minimum size for effective use in the treatment. The small particles of titanium having a diameter of 35 mesh have been found to be sufficiently usable. The small particles of titanium in the shape of shaving 2 to 4 mm in length and 1 to 2 mm in thickness have been found to bring about the nitriding satisfactorily. The other small particles of titanium in the shape of shavings having the dimensions shown in No. 6 and No. 7 have also been found usable. The nitride layers formed by the use of these small particles of titanium have been found to possess a desired color of nitride.

TABLE 3

| Example | Size of particles of titanium | Nitriding condition | | Phenomenon of combustion |
|---|---|---|---|---|
| | | Temperature | Duration | |
| No. 1 | 325 mesh | 800° C. | 4 hr | Immediate combustion on rise of temperature |
| No. 2 | 200 mesh | " | " | |
| No. 3 | 100 mesh | " | " | Occasional combustion |
| No. 4 | 35 mesh | " | " | No combustion (Hue: Good) |
| No. 5 | 2 to 4 mm (length) 1 to 2 mm (thickness) | " | " | No combustion (Hue: Good) |
| No. 6 | 5 mm (length) 0.2–0.5 mm (thickness) | " | " | No combustion (Hue: Slightly changed) |
| No. 7 | 10 mm (length) 0.2 to 0.5 mm (thickness) | " | " | No combusion (Hue: locally discolored) |

EXPERIMENT 4

Small particles of sponge titanium prepared in varying sizes were treated by the typical procedure of FIG. 1 under the nitriding conditions of 800° C. of temperature and 4 hours of duration. The results were as shown in the righthand column of Table 4. From this table, it is noted that the small particles of sponge titanium having such small diameters as 200 mesh and 325 mesh do not tolerate actual use because they undergo the phenomenon of combustion. It has been found, however, that the small particles of sponge titanium having a diameter of 100 mesh are usable despite their liablity to occasional combustion, indicating that this particular diameter constitutes the critical size for effective use in the treatment. Further, the small particles of sponge titanium having a diameter of 35 mesh have been found to be satisfactorily usable and the small parrticles of sponge titanium prepared in the shape of cubes of 2 mm as shown in No. 5 have been found to bring about quite satisfactory nitriding. The small particles of sponge titanium having other sizes shown in No. 6 and No. 7 have been found to be usable as well. The nitride layers obtained by the use of these small particles of sponge titanium which have proved usable assume a desired color of nitride.

TABLE 4

| Example | Small particles of sponge titanium | Nitriding condition | | Phenomenon of combustion |
|---|---|---|---|---|
| | | Temperature | Duration | |
| No. 1 | 325 mesh | 800° C. | 4 hr | Immediate combustion on rise of temperature |
| No. 2 | 200 mesh | " | " | |
| No. 3 | 100 mesh | " | " | Occasional combustion |
| No. 4 | 35 mesh | " | " | No combustion (Hue: Good) |
| No. 5 | Cubes of 2 mm | " | " | No combustion (Hue: Good) |
| No. 6 | Cubes of 6 mm | " | " | No combustion (Hue: Slightly changed) |
| No. 7 | Cubes of 12 mm | " | " | No combustion (Hue: Locally discolored) |
| No.8 | Cubes of 20 mm | " | " | No combustion (Hue: Locally discolored) |

Now, the apparatus to be used in performing the nitriding treatment on the surface of a shaped article of titanium by the method for nitriding the surface of a shaped article of titanium described above will be explained below.

Figure 3:
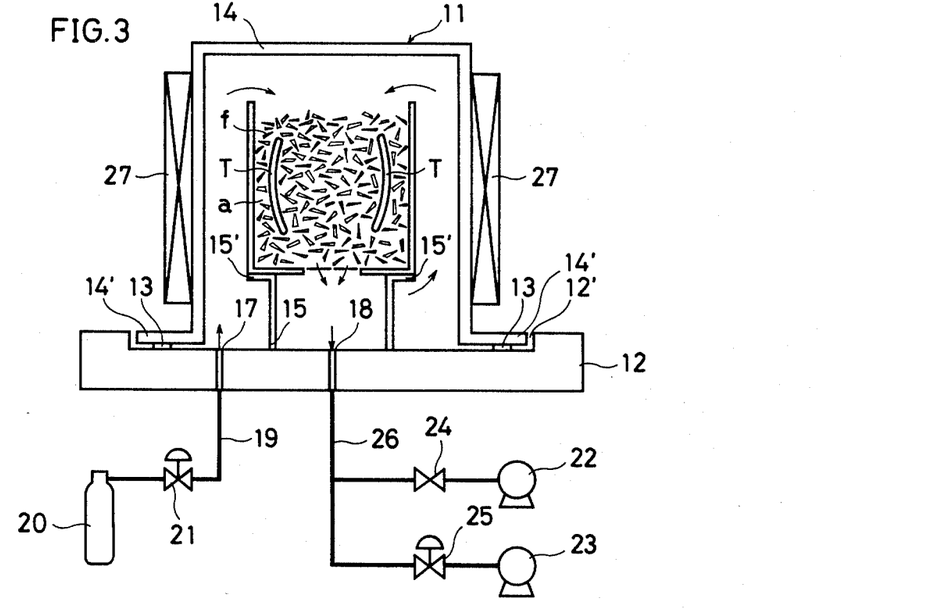
FIG. 3 is an explanatory diagram illustrating a typical apparatus for nitriding the surface of a shaped article of titanium according to the present invention.

FIG. 3 is an explanatory diagram of a typical apparatus for nitriding the surface according to the present invention. In a treating furnace 11, an outer tube 14 is formed by fitting a flange part 14' extended outwardly from the lower edge of a stoppered tubular member airtightly in a depression 12' formed on the upper side of a base plate 12 through the medium of a packing member 13. At the center of the base plate 12 inside the aforementioned outer tube 14, a supporting tubular member 15 having a flange part 15' extended outwardly from the upper periphery thereof is disposed. On the upper end surface of the supporting tubular member 15, a bottomed tubular member having an opening at the center of the bottom thereof is disposed to form an inner tube 16. Openings communicating with the ambient air are perforated in the base plate 12, one inside the supporting tubular member 12 below the inner tube 16 and the other between the outer tube 14 and the supporting tubular member 15, to serve respectively as an outlet 18 and an inlet 17. Thus, a continuous flow path is established, starting from the inlet 17, passing through the empty space intervening between the inner and outer tubes 16, 14, the interior of the inner tube 16, and the interior of the supporting tubular member 15, and ending at the in outlet 18. To the inlet 17 is connected a nitrogen gas cylinder 20 as a nitrogen gas feeding means through the medium of a pipe 19 fitted with a throttle valve 21. To the outlet 18 are connected a vacuum pump 22 and an evacuation pump 23 as vacuumizing means through the medium of a pipe 26 which is passed through a valve 24 and a throttle valve 25. Owing to this arrangement, therefore, the inner gas of the treating furnace 11 can be drawn out as required. Thus there is established a flow path for continuous supply of nitrogen gas from the nitrogen gas cylinder 20 to the interior of the treating furnace 11. A heating means 27 adapted to heat the interior of the treating furnace 11 to the temperature of treatment is disposed around the periphery of the outer tube 14 of the aformentioned treating furnace 11. In the present apparatus described above, the inner tube 16 is filled with small particles of titanium or titanium alloy to form a nitrogen gas filter f. At the same time, a shaped article T of titanium subjected to nitriding treatment is embedded in the mass of the aforementioned small particles of titanium or titanium alloy. In this setup, therefore, the mass of small particles of pure titanium or titanium alloy additionally serves as a shaped article supporting member, i.e. a part "a" for disposing the shaped article of titanium for the nitriding treatment. The nitrogen gas filter f and the shaped article disposing part "a" form an integral unit.

To put the apparatus of the foregoing description to use in the nitriding treatment of a shaped article of titanium, a shaped article T of titanium subjected to the treatment is embedded in the mass of small particles of pure titanium or a titanium alloy which fills the interior of the part "a" for disposing the shaped article of titanium for the nitriding treatment, concurrently serving as the nitrogen gas filter f. Then, the throttle valve 21 of the nitrogen gas cylinder 20 is kept closed and the vacuum pump 22 is actuated to evacuate the interior of the treating furnace 11 to a high degree of vacuum. Subsequently, the valve 24 is closed and the throttle valve 21 of the nitrogen gas cylinder 20 is opened to fill the interior of the treating furnace 11 with the nitrogen gas. The evacuation an the introduction of nitrogen gas into the treating furnace are cyclically repeated two or three times to expel as much residual air from the interior of the treating furnace 11 as possible. At the same time, the heating means are actuated to elevate the inner temperature of the treating furnace 11 to a prescribed level such as, for example, 700° C. to 880° C. Then the supply of nitrogen gas from the nitrogen gas cylinder 20 is continued with the throttle valve 21 connected to the cylinder 20 suitably controlled. The evacuation pump 23 is operated with the throttle valve 25 connected thereto properly controlled, to continue the flow of nitrogen gas under a reduced pressure of 300 to several Torrs and effect the nitriding treatment. The nitrogen gas being supplied from the nitrogen gas cylinder 20, passed through the inlet 17, and introduced into the treating furnace 11 is activated by being preheated by the heating means 27 disposed around the periphery of the outer tube 14. The activated nitrogen gas is first brought into contact and allowed to react with the small particles of pure titanium or a titanium alloy forming the nitrogen gas filter f inside the inner tube 16, with the result that the oxygen and hydrogen components present in the nitrogen gas are removed from the nitrogen gas through this reaction. The nitrogen gas, now in a purified state, comes into contact with the shaped article T of titanium and reacts with the surface of the shaped article and consequently forms a nitride layer on the surface of the shaped article t of titanium. Since the flow of the nitrogen gas is continued by the operation of the nitrogen gas cylinder 20 as supply means and the evacuation pump 23 as vacuumizing means, the shaped article T of titanium is exposed to fresh nitrogen gas and consequently is enabled to acquire a nitride coating of desirable quality. The pressure of the nitrogen gas during the course of this treatment is controlled in the range of 300 to several Torrs as mentioned above to ensure improvement of the surface of the nitride coating to be formed on the surface of the shaped article. This pressure is not always required to be limited within this range. The airtightness of the interior of the treating furnace 11 can be easily maintained by keeping the pressure of the nitrogen gas inside this furnace at a level slightly higher than the normal atmospheric pressure. As concerns the procedure of operation, at the outset of the nitriding treatment, the interior of the treating furnace 11 is evacuated to a high degree of vacuum by the operation of the vacuum pump 22 before the introduction of the nitrogen gas is started. Otherwise, the flow of the nitrigen gas through the interior of the treating furnace 11 is continued until the furnace 11 is filled solely by the nitrogen gas. The heating may be started ater the treating furnace 11 is filled solely with the nitrogen gas. Alternatively, the inner temperature of the treating furnace 11 may be elevated to the prescribed level in advance and the shaped article T of titanium may be inserted and the supply of the nitrogen gas started thereafter. In the present embodiment, the vacuum pump 22 and the evacuation pump 23 are used as vacuumizing means to ensure quick displacement of the inner gas of the treating furnace 11 with the nitrogen gas at the outset of the treatment and, at the same time, to permit easy adjustment of the flow of the nitrogen gas during the course of the treatment. The vacuum pump 22 and the evacuation pump 23, when desired, may be merged into one integral pump. When the interior of the treating furnace 11 is formed in a vertical double-tube construction as in the present embodiment, the activation of the nitrogen gas by preheating with the heating means 27 and the reaction of the activated nitrogen gas with the shaped article T of titanium can be carried out more efficiently. Optionally, the interior of the base plate 12 may be formed in a water-cooling construction.

The small particles of pure titanium or a titanium alloy to be used for the nitrogen gas filter f are required to size or shape such that they avoid commencing combustion on contact with the oxygen component in the nitrogen gas through the agency of heating. Since the nitriding generally begins at a temperature of about 700° C., the small particles of pure titanium or titanium alloy must be in a size such that they avoid commencing combustion on contact with the oxygen component in the nitrogen gas at this temperature. To be specific, this size is about 100 mesh. Further for the purpose of enabling the oxygen and hydrogen components present in the nitrogen gas to react more readily with the small particles of titanium or titanium alloy such as ferrotitanium used for the nitrogen gas filter f than with the surface of the shaped article of titanium, it is advantageous to fix the temperature of the nitrogen gas filter f at a level higher than the temperature of the shaped article disposing part "a". In this sense, more desirable results are obtained by using small particles of pure titanium or ferro-titanium having a diameter larger than 80 mesh. Only when the small particles of titanium to be used have such a large diameter as mentioned above, the otherwise inevitable combustion of the small particles on contact with the oxygen and hydrogen components in the nitrogen gas at a heating temperature higher than the temperature of the nitriding treatment on the surface of the shaped article of titanium can be effectively and amply precluded. Further where the nitrogen gas filter f and the shaped article disposing part "a" are disposed as merged, for the purpose of enabling the nitrogen gas to permeate the mass of the small particles of pure titanium or titanium alloy and come easily into contact with the shaped article of titanium, these small particles are desired not to be unduly minute, namely in a state enjoying sufficient perviousness to gas. In this sense, the small particles having a diameter larger than 60 mesh, specifically a diameter of 35 mesh or a size of about 10 mm, for example, avoid commencing combustion on contact with the nitrogen gas and warrant a long service life for the nitrogen gas filter f because the temperature of titanium at the beginning of nitriding is about 700° C. and the heat distorsion point of titanium is slightly below 900° C. As small particles of titanium, flakes, shavings, and sponges of pure titanium may be used. As small particles of a titanium alloy, small particles of ferro-titanium may be used.

Figure 4:
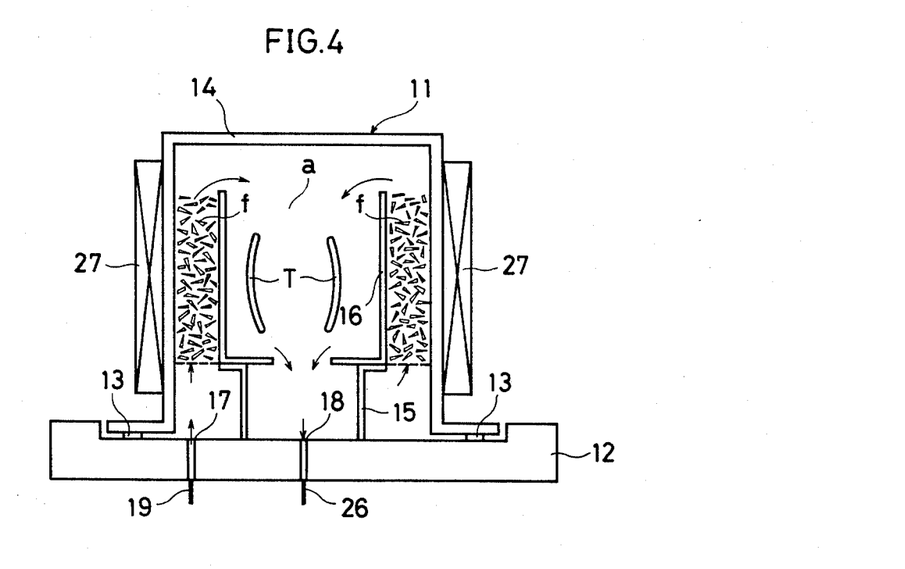
FIG. 4, FIG. 5, and FIG. 6 are explanatory diagrams illustrating other designs of the interior of treating furnace in the apparatus of FIG. 3.
Figure 5:
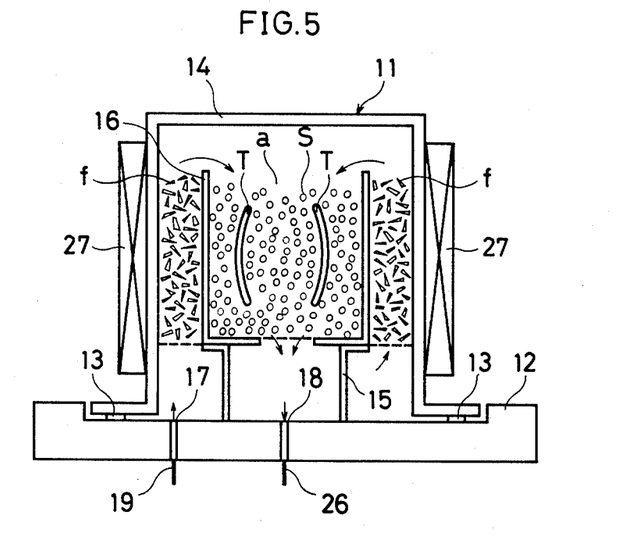

In the embodiment described above, the inner tube 16 serves as a combination of the nitrogen gas filter f and the shaped article disposing part "a". Alternatively, as illustrated in FIG. 4, the empty space intervening between the inner and outer tubes 16, 14 may be filled with small particles of pure titanium or small particles of a titanium alloy to form a nitrogen gas filter f and the interior of the inner tube 16 may be used as a part a for the disposition of the shaped article of titanium. In this case, when a granular, powdery, or fragmental member such as, for example, quartz beads or fragments are disposed as a supporting member s around the periphery of the shaped article T of titanium in the shaped article disposing part "a" as illustrated in FIG. 5, the nitrogen gas passes through the gaps separating the aforementioned quartz beads en route to the site of contact with the shaped article T of titanium. Since the nitrogen gas is enabled to come into uniform contact with the entire surface of the shaped article of titanium, the nitride layer formed on the surface of the shaped article acquires a surface of uniform quality. Thus, the treated shaped article of titanium is provided with a nitride coating of highly desirable quality. As the supporting member 5, granules, particles, and fragments of other substances such as alumina, ceramic, and Vycor glass (high-silica glass) which withstand at the temperatures of nitriding treatment about or above 700° C. to 880° C. may be used. In these materials, those which are porous and are liable to entrap gas in the pores thereof are excluded because the gas so entrapped comes into contact with the shaped article T of titanium under treatment and reacts with the surface of the shaped article and forms a coating other than the nitride layer on the surface of the shaped article of titanium.

Figure 6:
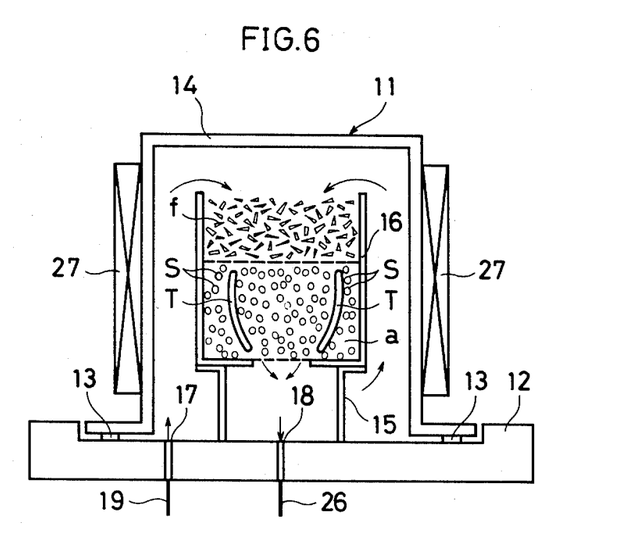
Figure 7:
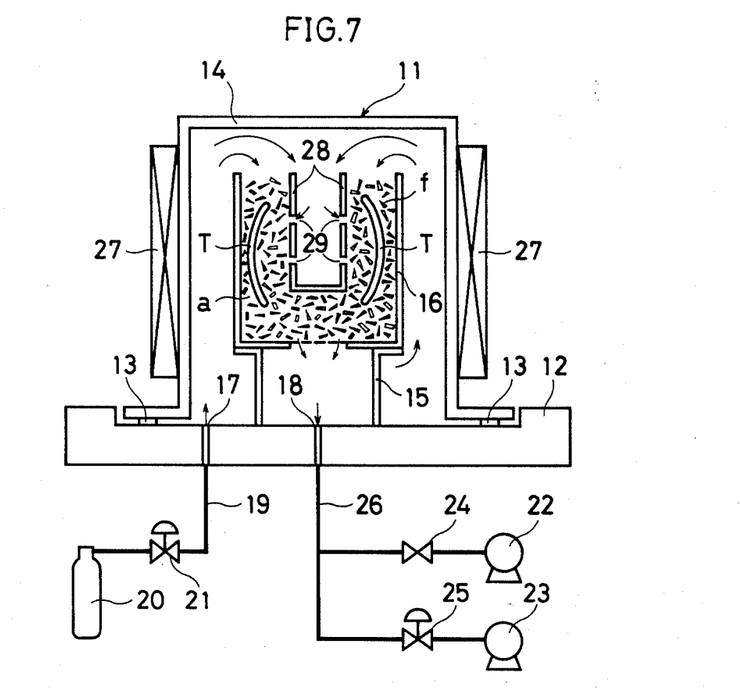
FIG. 7 is an explanatory diagram illustrating another typical apparatus for the nitriding treatment according to the present invention and FIG. 8 is an explanatory diagram illustrating another typical design of the interior of treating furnace in the apparatus of FIG. 7.
Figure 8:
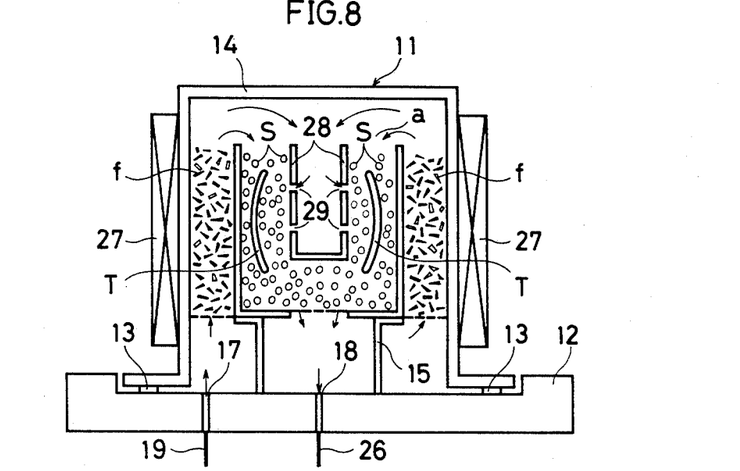

In the apparatus to be used in nitriding the surface of the shaped article of titanium as contemplated by the present invention, since the nitrogen gas is only required to permeate the nitrogen gas filter f en route to the site of contact with the shaped article T of titanium under treatment, the supporting member s may be disposed in the lower part of the interior of the inner tube 16 and the shaped article T of titanium under treatment may be embedded in the supporting member s to form a disposing part "a" as illustrated in FIG. 6. The small particles of pure titanium or a titanium alloy may be disposed as a nitrogen gas filter f on the shaped article disposing part "a". Otherwise, where the nitrogen gas filter f and shaped article disposing part "a" are disposed as merged as illustrated in FIG. 3, the inlet 17 and the outlet 18 may be used as mutual reverses and the nitrogen gas supply means may be connected to the opening 18 and the vacuumizing means to the opening 17 respectively to reverse the flow path for the nitrogen gas. When a bottomed inside tube 28 is additionally disposed as illustrated in FIG. 7 inside the inner tube 16 which is serving as the combination of the nitrogen gas filter f and the shaped article disposing part "a" as illustrated in FIG. 3 holes 29 are bored at suitable positions in the lateral wall of the aforementioned inside tube 28, this setup brings about an effect of further uniformizing the contact of the nitrogen gas with the shaped article T of titanium. Again in this case, the nitrogen gas supply means and the vacuumizing means may be connected as reversed. Optionally, as illustrated in FIG. 8, the nitrogen gas filter f and the shaped article disposing part "a" may be formed as mutually independent units by having the empty space between the inner and outer tubes 16, 14 filled with the small particles of pure titanium or titanium alloy and used as the nitrogen gas filter f and the interior of the inner tube 16 used as the shaped article disposing part "a". When the supporting member s such as quartz beads is disposed around the periphery of the shaped article T of titanium inside the inner tube 16 now serving as the shaped article disposing part "a", the contact of the nitrogen gas with the surface of the shaped article of titanium can be uniformized to a greater extent. Thus the nitride layer formed on the surface of the shaped article acquires a uniform surface.

Figures 9, 10:
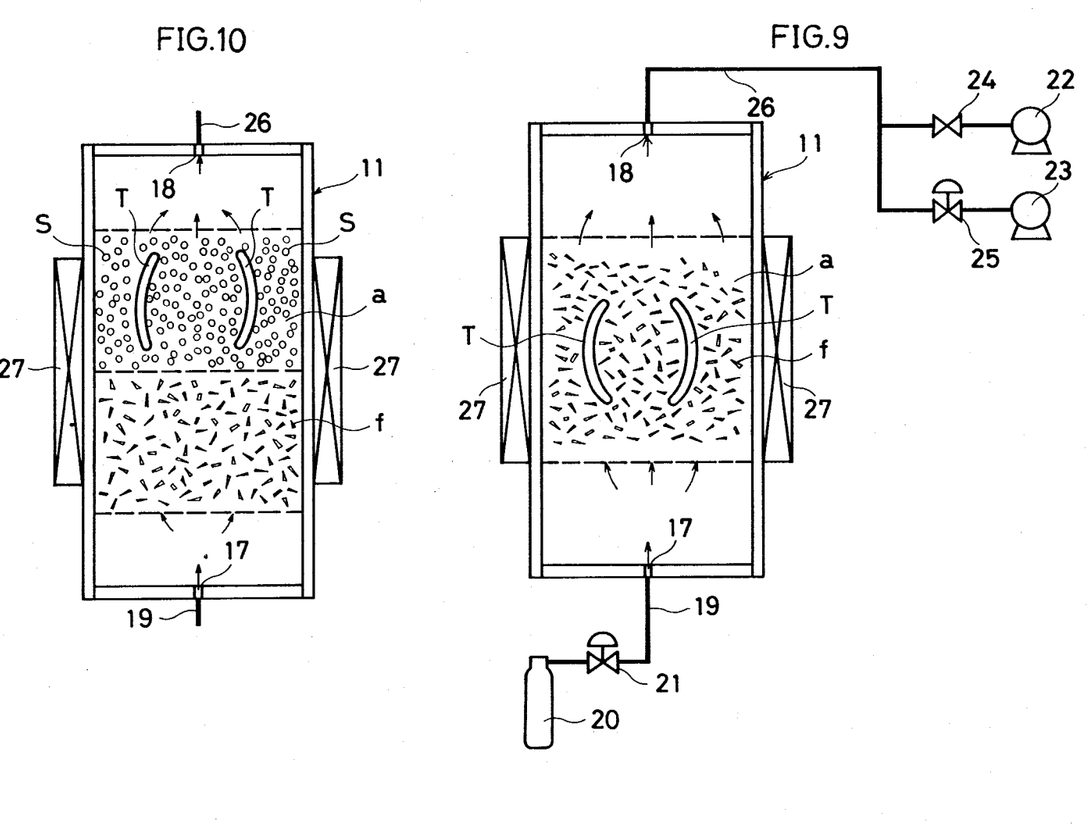
FIG. 9 is an explanatory diagram of the aforementioned apparatus adapted to use a straight tube as a treating furnace therein.
FIG. 10 is an explanatory diagram illustrating another typical design of the interior of treating furnace in the apparatus of FIG. 9.

One sole tubular member may be used as the treating furnace 11 as illustrated in FIG. 7 and FIG. 10. Also in this case, the nitrogen gas filter f and the shaped article disposing part "a" may be formed as merged and the small particles of pure titanium or a titanium alloy may be disposed around the periphery of the shaped article T of titanium under the treatment as illustrated in FIG. 9. Alternatively, the nitrogen gas filter f and the shaped article disposing part "a" may be formed as mutually independent units and quartz beads as the supporting member s may be disposed around the periphery of the shaped article T of titanium as illustrated in FIG. 10. In the setups illustrated in FIG. 9 and FIG. 10, the straight tubes are vertically disposed each as the treating furnace 11. They may be disposed, when necessary, in a horizontal posture. When the straight tube is horizontally laid, the flow of the nitrogen gas inside the straight tube as the treating furnace 11 is likely to lose uniformity in the upper part and the lower part of the interior of the tube. In this case, the contact of the nitrogen gas with the surface of the shaped article of titanium can be uniformized by either having the nitrogen gas filter f and the shaped article disposing part "a" formed in a merged state or having the supporting member s disposed around the periphery of the shaped article T of titanium under treatment. As the treating furnace, not only the aforementioned straight tube but also a U-shaped tube may be used effectively.

What is claimed is:

1. An apparatus for nitriding the surface of a shaped article of titanium, comprising a sole gas flow means extending between an inlet connected to a nitrogen gas supply means and an outlet adapted to effect discharge of a gas related to a vacuum means, a nitrogen gas filter comprising small particles of pure titanium or small particles of a titanium alloy and a part for disposing said shaped article of titanium for a nitriding treatment, said nitrogen filter and said shaped article disposing part being disposed either independently of each other or as superposed one over the other inside said gas flow means, and heating means disposed to serve one for said nitrogen gas filter and the other for said shaped article disposing part.

2. The apparatus of claim 1, wherein said sole gas flow means comprises a stoppered outer tube and an upwardly opened blind inner tube enclosed in said outer tube and forms a flow path consisting of an inlet opening into the interior of said outer tube, an opening intervening between said inner and outer tubes, the interior of said inner tube, and an outlet led out to said inner tube.

3. The apparatus of claim 2, wherein said inner tube further encloses therein an upwardly opened blind inside tube and said inside tube and said inner tube constitute themselves part of said flow path.

4. The apparatus of claim 1, said gas flow path is formed of one tubular member and said various means are disposed in series.

5. The apparatus of any of claims 1 through 4, wherein said part for disposing a shaped article of titanium for a nitriding treatment is filled with a granular, powdery, or fragmental member for supporting said shaped article of titanium inside said part and said shaped article of titanium is embedded in said supporting member.

6. The apparatus of claim 5, wherein granules, particles, or fragments of quartz are used as the supporting member for said shaped article of titanium.

7. The apparatus of claim 5, wherein said small particles of pure titanium or said small particles of titanium alloy are larger than 100 mesh.

8. The apparatus of claim 5, wherein said small particles of pure titanium or said small particles of titanium alloy are larger than 80 mesh.

9. The apparatus of claim 5, wherein said small particles of pure titanium or said small particles of titanium alloy are flakes of pure titanium or titanium alloy.

10. The apparatus of claim 5, wherein said small particles of pure titanium or said small particles of titanium alloy are shavings of pure titanium or titanium alloy.

11. The apparatus of claim 5, wherein said small particles of pure titanium or said small particles of titanium alloy are particles of sponge titanium.

12. The apparatus of claim 5, wherein said small particles are small particles of ferrotitanium.

* * * * *